US008515680B2

(12) United States Patent
Pipke et al.

(10) Patent No.: US 8,515,680 B2
(45) Date of Patent: Aug. 20, 2013

(54) ANALYSIS OF TRANSCRIPTOMIC DATA USING SIMILARITY BASED MODELING

(75) Inventors: Robert Matthew Pipke, Oak Park, IL (US); Jack E. Mott, Idaho Falls, ID (US)

(73) Assignee: Venture Gain L.L.C., Naperville, IL (US)

( * ) Notice: Subject to any disclaimer, the term of this patent is extended or adjusted under 35 U.S.C. 154(b) by 0 days.

(21) Appl. No.: 12/835,226

(22) Filed: Jul. 13, 2010

(65) Prior Publication Data

US 2011/0093244 A1   Apr. 21, 2011

Related U.S. Application Data

(63) Continuation of application No. 11/402,478, filed on Apr. 12, 2006, now abandoned.

(60) Provisional application No. 60/670,950, filed on Apr. 13, 2005.

(51) Int. Cl.
*G06F 7/00* (2006.01)

(52) U.S. Cl.
USPC ............. 702/19; 702/20; 703/11; 707/700; 435/6.1; 536/24.5

(58) Field of Classification Search
None
See application file for complete search history.

(56) References Cited

U.S. PATENT DOCUMENTS

| | | | |
|---|---|---|---|
| 4,937,763 A | 6/1990 | Mott | |
| 5,223,207 A | 6/1993 | Gross et al. | |
| 5,410,492 A | 4/1995 | Gross et al. | |
| 5,459,675 A | 10/1995 | Gross et al. | |
| 5,629,872 A | 5/1997 | Gross et al. | |
| 5,761,090 A | 6/1998 | Gross et al. | |
| 5,764,509 A | 6/1998 | Gross et al. | |
| 5,774,379 A | 6/1998 | Gross et al. | |
| 6,119,111 A | 9/2000 | Gross et al. | |
| 6,181,975 B1 | 1/2001 | Gross et al. | |
| 6,240,372 B1 | 5/2001 | Gross et al. | |
| 6,553,334 B2 | 4/2003 | Gross et al. | |
| 6,804,628 B2 | 10/2004 | Gross et al. | |
| 6,957,172 B2 | 10/2005 | Wegerich | |
| 6,999,899 B2 | 2/2006 | Gross et al. | |
| 7,003,403 B1 | 2/2006 | Dougherty et al. | |
| 2002/0055826 A1 | 5/2002 | Wegerich et al. | |
| 2002/0152056 A1 | 10/2002 | Herzog et al. | |
| 2003/0126258 A1* | 7/2003 | Conkright et al. | ............ 709/224 |
| 2003/0139908 A1 | 7/2003 | Wegerich et al. | |
| 2003/0158694 A1 | 8/2003 | Wegerich | |

OTHER PUBLICATIONS

Wagner et al. (Proteomics, vol. 3, p. 1692-1698, 2003).*
Piatetsky-Shapiro et al. (SIGKDD '03, Aug. 24-27, 2003, Washington, DC, USA., p. 407-415).*
Duch (Control and Cybernetics, vol. 29,No. 4, p. 1-29, 2000).*
Bicciato, Silvio et al,; "Pattern Identification and Classification in Gene expression Data Using an Autoassociative Neural Network Model"; Biotechnol Bioeng, vol. 81, p. 594-606. 2003.
Diaz, Ignacio et al.; "Residual Generation and Visualization for Understanding Novel Process"; Neural Networks, 2002, IJCNN '02. Proceedings of the 2002 International Joint Conference on, vol. 3, p. 2070-2075, 2002.
Hastie, Trevor et al.; "Local Regression: automatic Kernel Carpentry"; Statistical Science, vol. 8, No. 2, p. 120-143, 1993.
Eisen, Michael ; "Cluster and Tree View Manual," Copyright Stanford University 1998-99 (20 pages).
Lahner et al., "Genomic scale profiling of nutrient and trace elements in *Arabidopsis thaliana*," Nature Biotechnology, Oct. 2003, vol. 21, No. 10, pp. 1215-1221.
Möller-Levet, Yin, Cho and Wolkenhauer, "Modelling Gene Expression Time-Series with Radial Basis Function Neural Networks," Proceedings 2004 IEEE International Joint Conference on Neural Networks, Jul. 25-29, 2004, vol. 2, pp. 1191-1195.
Pochet, DeSmet, Suykens and DeMoor, "Systematic benchmarking of microarray data classification: assessing the role of non-linearity and dimensionality reduction," Bioinformatics, Oxford University Press 2004, vol. 20, No. 17, pp. 3185-3195.
Silicon Genetics, Inc.: "Class Prediction (Predict Parameter Value)," Silicon Genetics 2002, pp. 1-11.
Singh et al., "Gene expression correlates of clinical prostate cancer behavior," Cancer Cell, Mar. 2002, vol. 1, pp. 203-209.

* cited by examiner

*Primary Examiner* — Mary Zeman
(74) *Attorney, Agent, or Firm* — Fitch, Even, Tabin & Flannery LLP

(57) ABSTRACT

An analytic apparatus and method is provided for diagnosis, prognosis and biomarker discovery using transcriptome data such as mRNA expression levels from microarrays, proteomic data, and metabolomic data. The invention provides for model-based analysis, especially using kernel-based models, and more particularly similarity-based models. Model-derived residuals advantageously provide a unique new tool for insights into disease mechanisms. Localization of models provides for improved model efficacy. The invention is capable of extracting useful information heretofore unavailable by other methods, relating to dynamics in cellular gene regulation, regulatory networks, biological pathways and metabolism.

21 Claims, 11 Drawing Sheets

*Fig. 11*
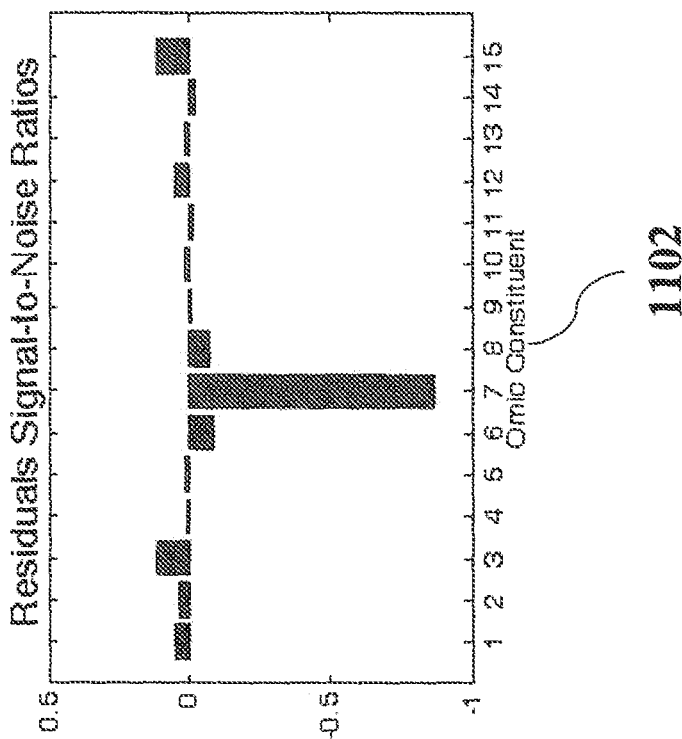
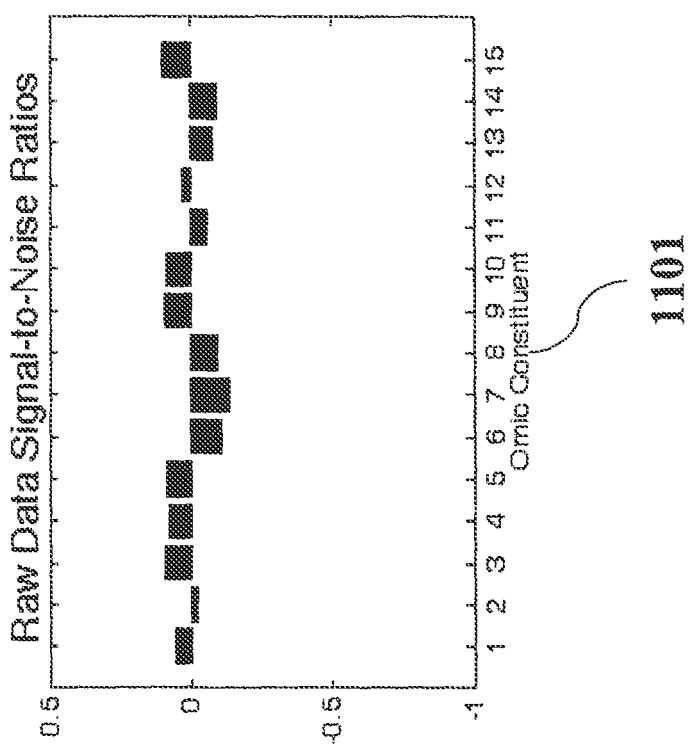

ANALYSIS OF TRANSCRIPTOMIC DATA USING SIMILARITY BASED MODELING

CROSS REFERENCE TO RELATED APPLICATIONS

This continuation application claims the benefit of priority under 35 U.S.C. §120 to prior U.S. Non-Provisional patent application Ser. No. 11/402,478 filed Apr. 12, 2006 now abandoned, which claims benefit of priority to Provisional Application Ser. No. 60/670,950 filed Apr. 13, 2005, which is fully incorporated herein for all purpose.

FIELD OF THE INVENTION

The invention relates to biomarker discovery and disease diagnosis and prognosis, especially based on transcriptomic data such as gene expression levels and proteomics.

BACKGROUND OF THE INVENTION

Recent advances in the biological sciences have made it possible to measure thousands of gene expression levels in cells using microarrays, and to quantify the cellular content of thousands of types of proteins using e.g., mass spectrometry, in single experiments with one sample of tissue or serum. Gene expression molecules, i.e., messenger RNA, and the proteins encoded by the mRNA comprise the "transcriptome" of the cell, the components of the cell that are the direct products of the transcription (the genome) and translation (the proteome) of DNA. Analysis of the transcriptome offers the potential to identify "bad actors" in the genetic expression process that are responsible for disease, and may offer both a signature for disease diagnosis, as well as targets for disease amelioration, whether through drugs or other means. By measuring thousands of components at once, the pace of biomarker discovery can be greatly accelerated, and the interactions between multiple components can be analyzed for complex disease mechanisms.

Genomic expression data representing semi-quantitatively the amount of mRNA present in a cell by on a gene-by-gene basis, may reveal markers for disease as well as patterns of expression that effectively differentiate or classify disease states and progression. Similarly, quantification of the count of proteins in the cell by protein molecule type, provides further insight into the overall regulation of the cell from DNA to protein product, and provides key insight into "post-transcriptional modifications" whereby protein structures are modified after translation from RNA. Pattern matching unknown patient samples against known microarray expression level patterns of disease state, may provide diagnosis or prognosis. Disease differentiation is key to applying the appropriate treatment. Cancers may manifest as seemingly similar phenotypes in identical tissue, yet have very different prognoses and treatment outcomes, because the biological pathway of disease is in fact different at the genetic level. It is essential to be able to identify what form of disease a patient has. Another useful application utilizing this kind of data is classifying patients as to whether they are candidates or not for the use of a drug which may, in a small subpopulation, have adverse effects related to the genetic makeup of the individual.

This new wellspring of genomic and proteomic data presents many challenges to discovery of the important information buried therein. One of the challenges of this data is the high dimensionality and the relative scarcity of patient observations. Often, thousands of gene expression levels are measured by a single microarray applied to patient tissue or a cell culture, but the total count of patients may be less than 20. Each such patient represents an observation of a vector comprising these thousands of expression levels. Another challenge is that the data can be extremely noisy, confounding complex analysis approaches that are sensitive to bad input. Yet another challenge is that the new measurement technologies are very sensitive to methodology, resulting in vastly different results when prepared by different researchers. Microarrays themselves have yet to be standardized, and microarrays from different manufacturers often have different oligonucleotide probes for the same gene, introducing variability due to oligo length or affinity. Yet another challenge is that the data often represents a mere snapshot of transcriptomic content, which is in a constant state of flux, as cellular genetic expression changes to adjust to the cell's needs and environment.

A number of methods are known for analysis of genomic and proteomic data. According to one known method, genetic expression levels for genes are compared across samples of normal tissue and diseased tissue, and where differential expression is sufficiently large, the gene is identified as a possible biomarker of the disease. This method is intended to identify gross amplification of a gene, or the complete silencing of a gene. According to known clustering methods, pair-wise correlations of the expression levels of pairs of genes are calculated, and genes are arranged in clusters according to a ranking of their pair-wise correlation across a number of samples. According to an approach that uses Support Vector Machines (SVMs), an optimal separation boundary with maximum margin (or maximum soft margin) is generated (possibly in higher dimensional space) for multivariate expression levels from two classes (normal and diseased), thus providing a classifier for future patterns.

However, these methods have their shortcomings. Gross differential expression analysis assumes static expression levels, and is easily confounded by expression dynamics. Furthermore, many diseases may be the result of more subtle deviations in expression than is typically tolerated by differential expression studies. Clustering only takes advantage of correlative information between pairs of genes, and thus misses more complex interactions and multi-gene dynamics. SVMs can be very computationally intensive, and produce optimal solutions that may overfit the typically small sample size, and as a consequence do not generalize well.

What are needed are improved analytic methods capable of tapping into the dynamic information in multivariate transcriptomic data, to reveal more subtle signatures for classification and data mining of biomarkers. Further, what are needed are faster methods that can be used interactively by discovery personnel, to provide leverage to extensive expertise in the exploration and discovery process. Further, methods are needed that are robust to the noisy nature of the transcriptome data, so that information can be derived from data from today's level of accuracy in microarray and mass spec measurement technologies.

SUMMARY OF THE INVENTION

The present invention provides a unique and advantageous model-based approach to analysis of genomic, proteomic, and general transcriptomic data, for diagnostics, prognostics and biomarker discovery. Accordingly, each patient sample is treated as an input vector, and gene expression levels are treated as variables. A set of patient data for known disease states is used to train a model, ideally a similarity-based model; thereafter, the model can be used to classify disease state, differentiate cancer types, determine candidacy for use of a drug or therapy, etc.; or can be used to model data from another class of tissue or serum sample, to provide insight into which components deviate and are thus potential markers for the disease mechanism.

Unlike conventional methods, which generally rely on statistical approaches and can only detect gross changes on the assumption of relatively static genetic expression, the present invention is capable of detecting both static expression level changes as well as deviations in dynamic behavior. Living cells are mostly dynamic systems, expressing and then turning off genes in complex regulation networks and biological pathways involving tens or hundreds of factors, in response to the metabolic needs of the cell. Disease most often occurs when these delicately balanced networks are upset and misregulated. Such an event can occur, for example, when a mutation occurs in a gene that produces a protein for regulating other, downstream genes. Since the gene product—the regulating protein—may no longer function, downstream regulation is impacted, with cascading effects. The present invention is capable of detecting these upset dynamics.

The invention takes the form of software for analysis of data. The software can run on any conventional platform, and can even be deployed in a remote, served environment, such as over the internet, because the needed data files can be sent to the processor for processing, and the results returned at a later time. However, a particular advantage of the present invention is that it has a small computing footprint and processes data quickly, making it ideal for an interactive tool, or for embedding in a distributed product for diagnostics (e.g., a CDROM deployed with a diagnostic microarray).

In a first embodiment of the invention, a model is trained with multivariate transcriptome profiles representative of normal health, and the model is then used to detect deviations in transcriptome patterns and dynamics representative of a diseased state, which deviations point to underlying disease mechanisms. An autoassociative model of gene expression data for normal tissue is trained from normal tissue data. A new input vector representing expression level data from diseased tissue is modeled with this model to provide an autoassociative estimate of the expression levels, which is then differenced with the actual measurements to provide residuals. A residual threshold test detects gene expression levels that are abnormal, identifying these genes as potential markers. Furthermore, the residual pattern can be pattern matched against stored patterns for known disease types to classify the input vector vis-à-vis disease.

In a second embodiment of the invention, a diagnostic classification is made for a dynamic multivariate genomic or proteomic profile. An inferential model is trained to recognize normal and diseased state transcriptome profiles, and new samples are analyzed and classified accordingly.

The classification capability of the invention can advantageously be extended to prognostics, or assessing the progression of a disease. Thus, in a third embodiment of the analytic method, especially useful for multi-class classification though also useful for binary classification, an autoassociative model is built for each class represented, containing only samples/observations from that class (and none that are not from that class). A new input observation to be classified is modeled by all models in the system, and an autoassociative estimate is produced from each. Each estimate is then pattern matched to the input vector to provide a "global similarity" score: The estimate vector is compared to the input vector using the similarity operator, and the vector similarity score represents the global similarity. The model that generates the estimate with the highest global similarity score represents the class of the input vector.

An important aspect of the present invention is the use of a kernel-based model, and more particularly a similarity-based model. Such models are capable of learning complex dynamic relationships from data, with a small and fast computing footprint, and are robust to noise in the input. Even more particularly, the model can be a localized model, which is reconstituted with each new input sample, thus filtering out less relevant learned profiles.

DESCRIPTION OF THE DRAWINGS

FIG. 11 is a signal-to-noise bar chart resulting from the analysis in FIG. 10.

DETAILED DESCRIPTION OF THE INVENTION

Figure 1:
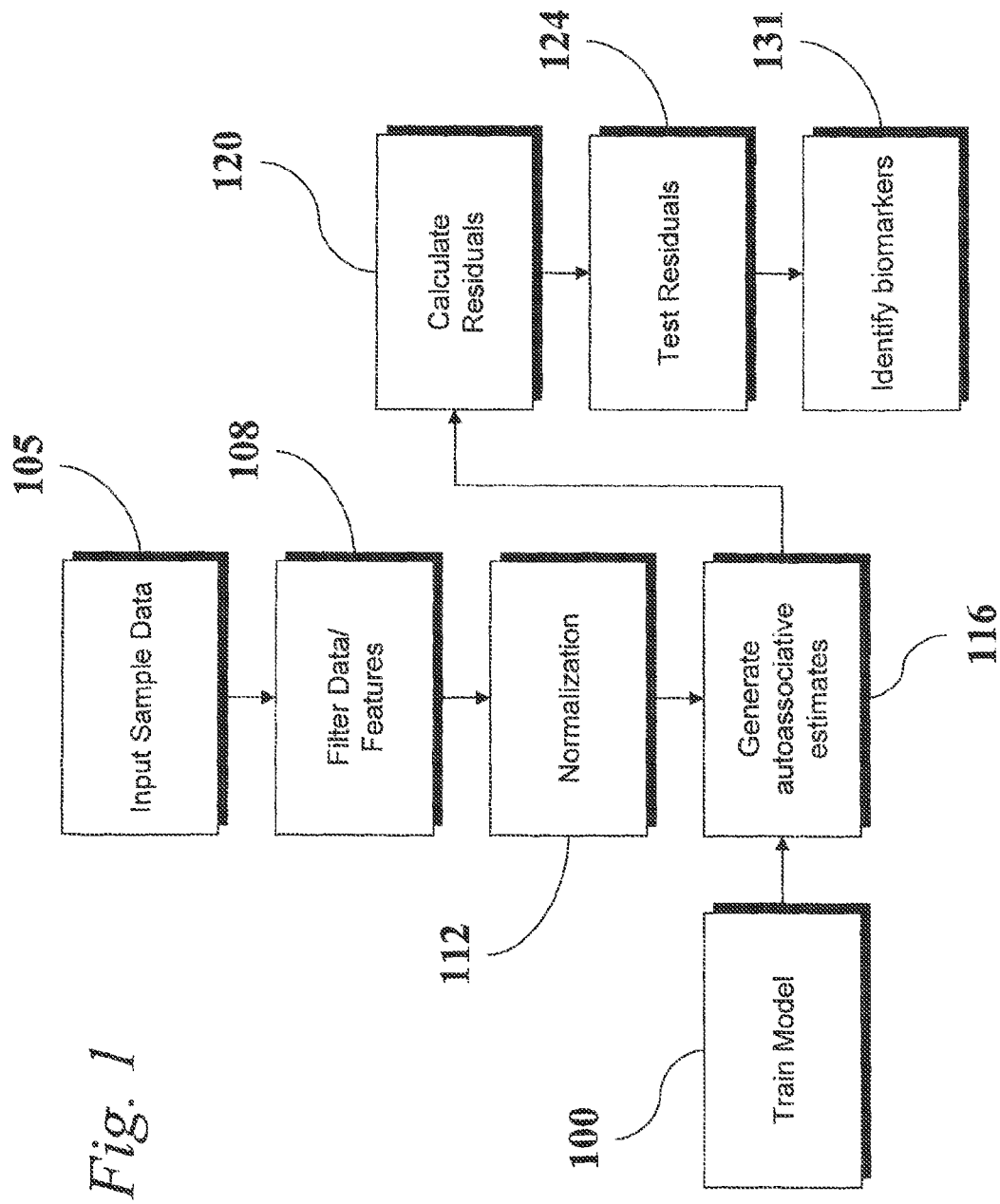
FIG. 1 is a flowchart of an aspect of the present invention for exploring genomic, proteotnic or metabolomic data.

The present invention can be used to analyze data from the transcriptome, e.g., genomic expression data or proteomic data, to provide diagnostic and prognostic information, or to provide biomarker discovery information, among other things. Genetic expression level data can be obtained using a number of methods known in the art, including microarrays, and generally can comprise raw expression level information or processed comparative expression level data, e.g., from two-color experiments. In brief, a microarray comprises a plurality of probes fixed at isolated locations on a substrate. Each probe is specific to a nucleotide sequence, usually known to correspond to at least a part of a known gene. Each probe location has a different probe on it, and the probe location itself may comprise thousands to hundreds of millions of identical oligonucleotides anchored to the substrate. When DNA from a sample (e.g., processed biopsy tissue or blood serum) is exposed to the microarray, sample DNA molecules having complementary genetic sequences to the oligonucleotides will specifically attach, or hybridize, with the matching probe. Labeling of the sample DNA allows for fluorescent imaging of the washed microarray, and reveals the amount of sample DNA that hybridized with probes at each location. This image information can be converted to expression level values. Assuming the amount of DNA obtained in the processing of the sample tissue or serum corresponds to the actual amount in the cells of that sample, and assuming that hybridization occurs with statistically equal likelihood for all oligonucleotide probes, the microarray data should provide a reasonable estimate of the expression levels for each gene in the cells of the sample, that are targeted in the microarray. A microarray can have any number of genes represented on it, which may or may not be comprehensive of the genes active in the cells of the sample.

Alternatively, quantification of protein content of cells or extracellular fluids from tissue and serum samples can be obtained from known methods such as mass spectrometry. In mass spec, the sample's protein contents are separated through any of a number of possible methods, introduced into the mass spec, and a mass-to-charge pattern is obtained which can be identified as specific proteins. The strength of the signature can be equated to protein levels in the sample.

Other cellular or extracellular content levels are also subject to measurement techniques known in the art, such as measurement of "metabolomic" components such as sugars, ions, and the like, and all such data can be used in the present invention, either separately or in combination. For example, a disease mechanism may be revealed by utilizing data from both protein content and gene expression levels in combination in the present invention. As another example, a disease diagnostic signature may best be differentiated utilizing metabolomic and proteomic data in the present invention. For purposes of the description of the present invention, "expression level" will be used, but should be taken to mean quantified data regarding cellular or serum components of any kind, not just genomic expression, unless otherwise specifically indicated.

The present invention advantageously utilizes empirical modeling to provide information from genomic, proteomic, and metabolomic data. An empirical model is "trained" using data gathered at a model development stage, and then the model is used to process a new sample to provide a diagnosis or prognosis, or alternatively, the model is used to process a different class or classes of samples to reveal mechanisms responsible for the differences between the class samples, e.g., normal from disease, or cancer of one molecular mechanism from cancer of a second molecular mechanism. The present invention uniquely provides a model that itself need not be derived from scientific information of biological pathways or mechanisms, but rather is purely data driven. Furthermore, the use of a model provides insights not afforded with conventional statistical techniques that may not be able to make use of dynamic data effectively.

Turning to FIG. 1, a flowchart is shown of an aspect of the present invention for use in exploring genomic expression data and the like, to identify deviations in gene expression levels and protein levels. Such information is potentially extremely useful for revealing disease mechanisms and possible intervention targets. Not only can the invention detect changes in gross expression and product levels (e.g., amplification), but also deviations in normal dynamics of expression, even when those deviations do not represent gross changes in expression level, but are within the normal range of expression. Accordingly, an empirical model is first trained in step 100, using data from a plurality of samples of normal expression, or expression in a first class of samples such as a first type of a cancer. Model training is discussed in detail below.

In step 105, expression level data from samples of the same class or a second class, e.g., diseased or cancer type 2, is provided. This data should correspond to the same components measured and modeled in step 100. Each sample represents equivalently a vector of readings of expression level, one vector element per component measured; furthermore, each sample typically will be taken from a unique tissue section or patient, although time series samples from a single patient are also contemplated hereunder.

In optional step 108, the input sample data can be culled down to a subset of data based on filtering or feature selection. For example, though expression level data for 10,000 genes may be provided in step 105, this may be reduced to 100 or 500 or 1000 select feature genes in step 108. A number of techniques are known in the art for selecting genes as "features" of a larger set of data, including selecting genes based on their signal to noise ratio. In the signal-to-noise ratio test, the expression level readings for a gene for one class of samples (e.g., normal) provides a mean expression level and a standard deviation in expression level. The same mean and standard deviation are calculated for data for that gene from samples from a second class of data. The gene's signal-to-noise (S2N) ratio is equal to the difference of the means divided by the sum of the standard deviations:

$$S_L = \frac{\mu_1 - \mu_2}{\sigma_1 + \sigma_2} \quad (1)$$

where $\mu$ represents the mean expression value for gene #L across patient samples from class 1 and class 2, respectively, and $\sigma$ represents the standard deviation in expression values for the gene across patient samples from class 1 and class 2 respectively. Class 1 may represent expression levels measured in normal tissue, while class 2 represents expression levels from diseased tissue. The signal-to-noise scores $S_L$ can be ranked. Typically, the informative genes are those with the highest absolute value. S2N indicates how much a gene expression level changes, on average, between the classes of sample, as conditioned by their respective noise levels.

In optional step 112, the input sample data may be normalized. Normalization of genetic expression or protein content data typically means normalizing across all genes or proteins for a given sample. This may be necessitated by the fact that each microarray experiment or spectrometer often has its own baseline of level measurement, which is not easily compared from microarray to microarray or spectrometer run to spectrometer run. It is desirable then to normalize each gene expression level vis-à-vis the expression levels of the other genes from that same sample. One method for normalizing is to calculate the mean expression level and standard deviation across all the genes (or constituents) of a sample; then scale the expression levels with the mean set to zero, and the standard deviation set to some constant, e.g., one. Whatever normalization method is used on the training data from which the model was created in step 100 should be applied to the data in this step 112.

In step 116, the model is used to generate autoassociative estimates of the expression level data in response to inputting the input sample. In autoassociative estimation, each input variable is also an output. The input in this case is the vector of all expression levels for a sample; the output is an estimate of what the model says the value should be, based on the input, and may differ from the input values. Accordingly, a wide variety of modeling techniques can be used, and are discussed below in detail. For each sample vector input, there should be a sample estimate.

In the alternative, an inferential model may also be used for this step 116, whereby additional estimates are generated in the model that are not present as inputs. For example, the input vector of constituent expression levels or quantities can comprise some of the constituents of a biological regulatory network, and the model can estimate the expression levels or quantities of other constituents of the biological regulatory network there from. In order for the model to be capable of this, the model is trained with reference data comprising both the variables that will serve as inputs, as well as the variables that will be inferred as estimates.

In step 120, the autoassociative estimates are differenced with the actual input values to produce "residuals". If an inferential model is used, while the actual measurements for constituents or components for which inferential estimates are generated are not inputted to the model, they are used at this point to form a difference with the model estimates. In step 124 one or more tests are performed on the residuals to provide information as to which genomic or proteomic components are deviating, thus identifying potential biomarkers of disease or intervention targets. The steps described above can be performed for all samples in each of the two classes, including the class that the model was trained on, to provide comparative residual information for step 124. Hence, the model is trained on data from class 1, and further provides estimates and residuals for data from class 1 (for example, with test data from that class, or on a leave-one-out modeling basis); then that same model is used to provide estimates and residuals for class 2 data.

Accordingly, one test that may be applied to the residuals is to calculate the mean of the residual for each genetic/proteomic component of the input, and compare the shift in means between one class and another. Typically, if there is no deviation in the behavior of a component, the residual mean will be close to zero, whereas it will be biased if behavior has changed. Components in which the residual mean has shifted substantially are identified as potential biomarkers, because their residuals have become pronounced when testing with data from a second class in a model built from the first class.

An extension of this mean shift test is to calculate a residual signal-to-noise ratio, as described above for raw signals: The difference in residual means between the two classes is divided by the sum of the residual standard deviations of the two classes. This conditions the shift in the mean by the apparent noisiness of the residuals.

Yet another test is to examine the standard deviation of the residuals of the two classes, and look for significant changes. This is useful when the mean of a residual may remain around zero, but a change in expression behavior is evidenced by an increase in standard deviation.

Given that microarray data can be very noisy, and the dynamics of the samples quite volatile, yet another residual test, called normalized cumulative residual, which can be applied is to sum the absolute value of the residuals for each component, and divide by the range of the expression level data for that gene.

Figure 2:
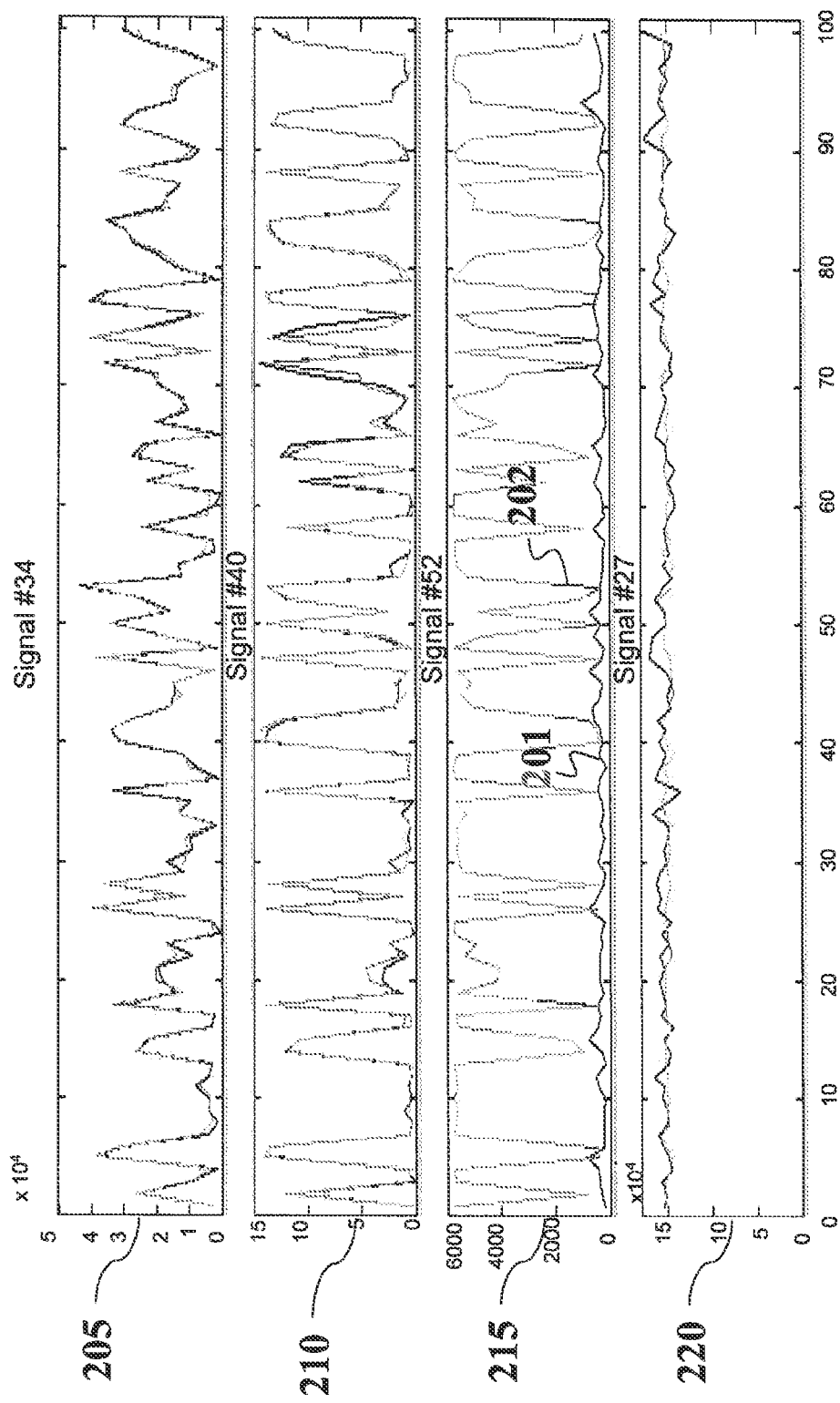
FIG. 2 is a set of charts for four simulated omic components, with original values in blue, and model-based estimates of same in green.

Results of the estimation process can also be viewed interactively by a researcher to see where deviations occur between actual expression levels and estimated expression levels. A software tool can be provided that shows these differences graphically, and allows a researcher to compare different sets of samples, or different selected features. Turning to FIG. 2, four plots are shown of estimated and actual expression levels from a genomic expression level simulator representing "patient samples" from a diseased class, as modeled by a model trained on normal class data only. Across the X-axis of each plot is the sample number (patient) from which an input vector of expression level data was obtained. Each plot represents one genetic component of the expression panel. The Y-axis in each plot represents the expression level of that genetic component (e.g., an mRNA level as measured by a microarray). Each plot comprises two lines: One is the set of actual expression levels (e.g., line 261), and the other (e.g., line 202) is the set of model-estimated expression levels. There are of course many more genetic components that were modeled in this case than the four that are shown. Signals 205 and 210 show a high correspondence between actual expression levels and estimates from the model, such that it is difficult to see the difference between the estimate line and the line for actual values. Furthermore, it can be seen that each patient or each sample has a different level of expression, being a snapshot in time of a dynamic system. Nonetheless, the model estimates the value relatively faithfully. Genetic component 215 however shows massive deviation between the levels of the samples from this class, and the estimates generated by the model, which show the high dynamism of the other genetic components. Here, the gene in question has turned off for the diseased patient samples, which is anomalous compared to the dynamic expression levels expected. This would be far more difficult to see on a purely statistical basis. Meanwhile, genetic component 220 represents a relatively non-dynamic gene, which is "on" for all patients of both the normal and diseased classes, with an overlay of noise.

Example

Figure 10:
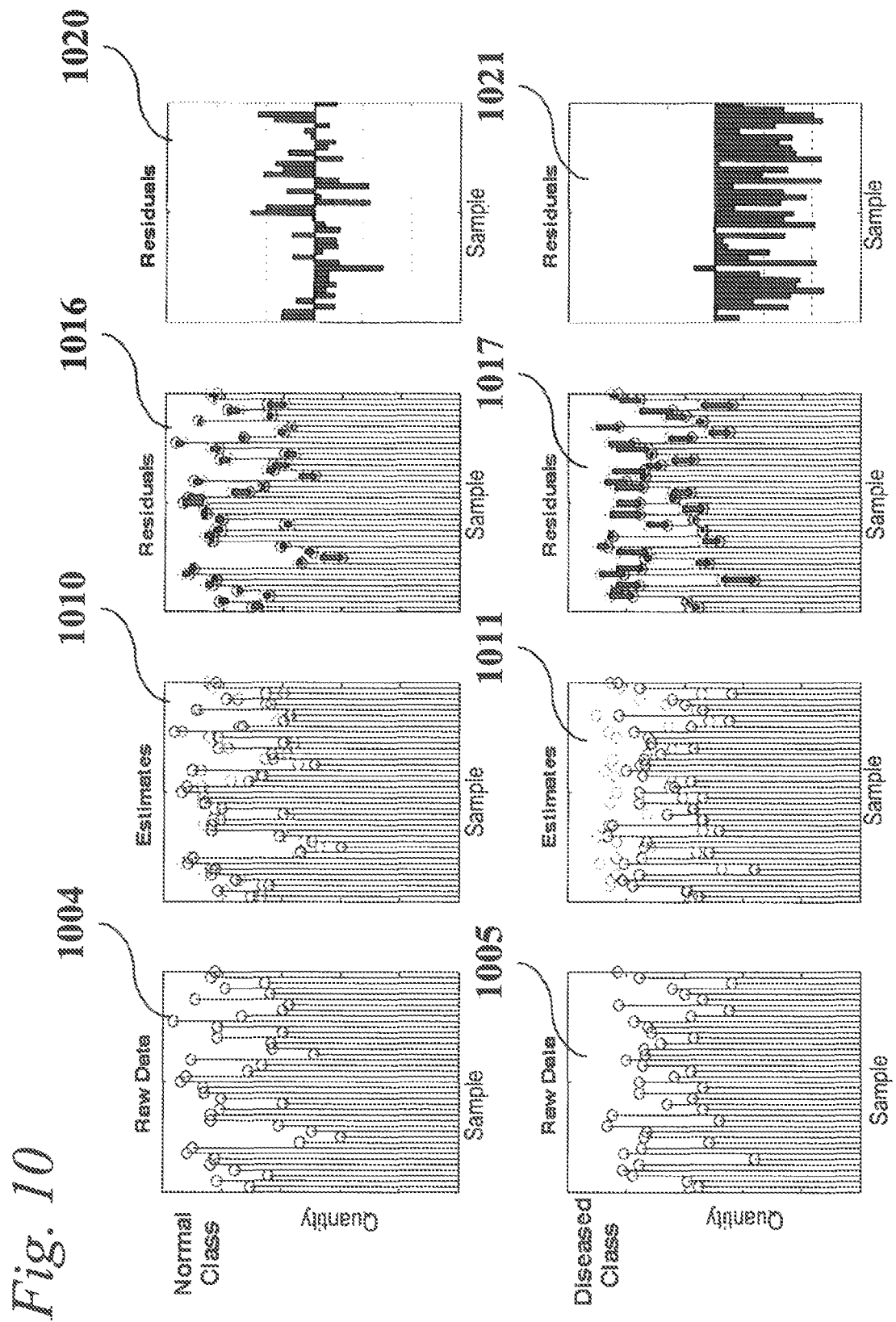
FIG. 10 is a set of stem charts showing results at each step of a method according to the invention for analysis of omic constituents between healthy and diseased classes of samples.

A simulated system comprising 15 constituents was developed whereby the 15 constituents related in their dynamic behavior to one another with varying degrees of linkage, emulating a regulatory network in a metabolic system. A set of reference data for this system, comprising observations of the 15 variables throughout various states of the dynamics of the system, was used to train a kernel-based model. Then, sets of normal and diseased observations, respectively, were generated, wherein one of the 15 constituents was perturbed to be slightly lower than it should be, regardless of its raw value. Turning to FIG. 10, a chart 1004 shows the value (quantity, expression level, etc.) for the suspect constituent, for the set of normal test observations. Each stem is a separate measurement of that constituent from the set of observations of "normal" specimens. Similarly is shown in chart 1005 the values for that same constituent in the set of observations of the "diseased" specimens. Values for the other 14 constituents are not shown in any of the charts of FIG. 10. In chart 1010, the estimated values for the suspect constituent are plotted on top of the actual values for normal specimens, generated by the trained model responsive to inputting the normal observations (estimates for the other 14 constituents are not shown, but were generated by the model). Similarly, in chart 1011, estimates for the suspect constituent are shown for the diseased specimens. In chart 1016, a bar is shown indicating the difference (residual) between the estimate and the actual measurement for each sample for the suspect constituent in the normal specimens, with a parallel chart for the diseased specimens shown in chart 1017. Finally, the residuals are shown in bar charts 1020 and 1021 for normal and diseased specimens respectively. As can be seen, though all of the diseased specimens had values for this constituent in chart 1005 that were not extraordinary and indeed were well within the typical expected range for the constituent (as can be seen by a comparison to the normal specimens in chart 1004), the residuals across all samples show a decided pattern in chart 1021 of being lower than expected. Turning to FIG. 11, the signal-to-noise ratios for each of the 15 constituents in the diseased specimens are shown in chart 1101, wherein it can be seen that constituent #7 (the perturbed constituent) does not particularly stand out. However in chart 1102, which displays the signal-to-noise ratios for the residuals generated using the model, the suspect constituent #7 is readily identified as a "bad actor" and is therefore a candidate biomarker of the diseased state.

Figure 9:
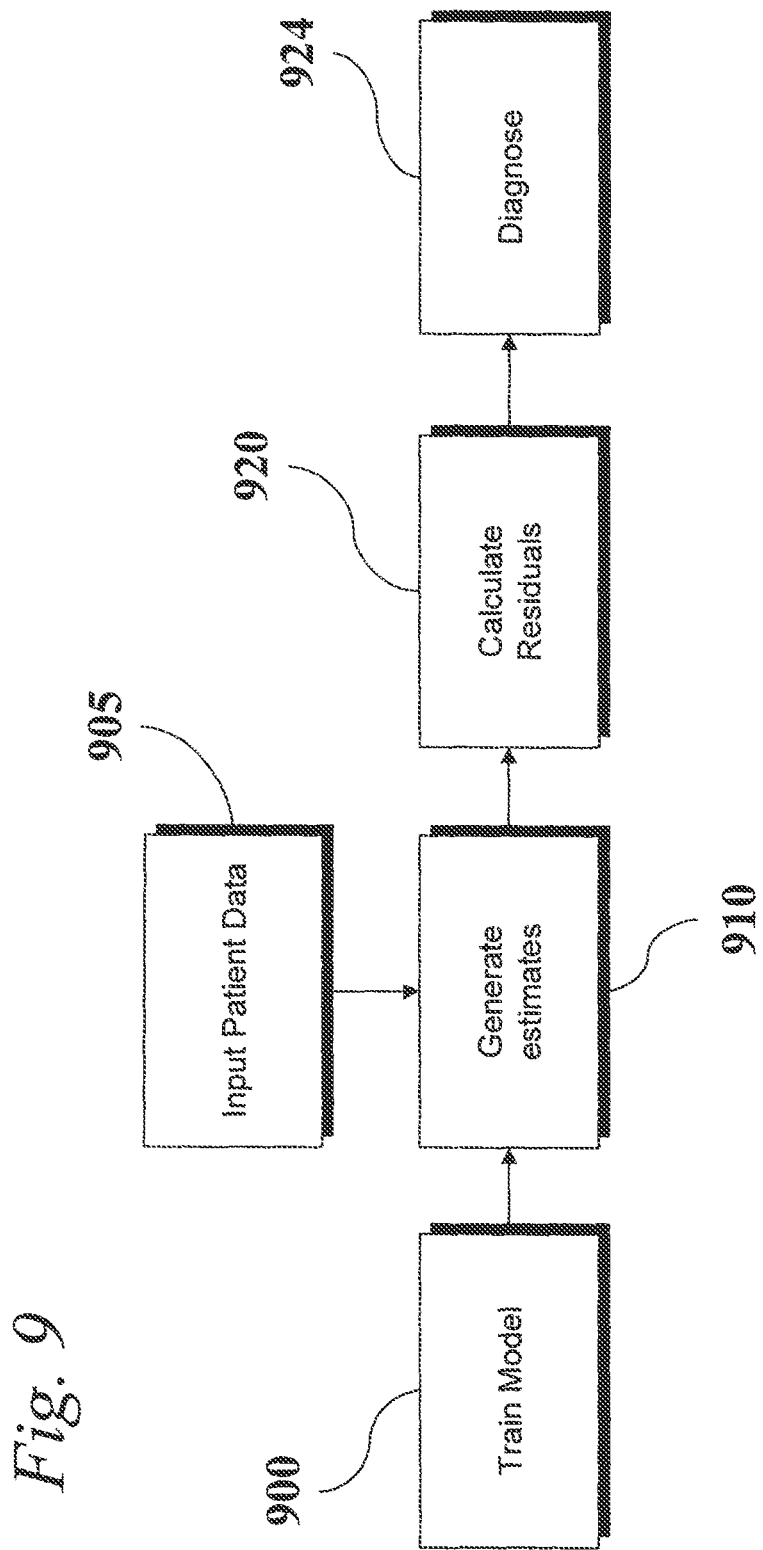
FIG. 9 is a flowchart of a method according to the invention for diagnosing disease from residuals generated from model-based estimates of omic constituents.

Further according to the invention, with reference to FIG. 9, residuals generated in the above-described manner can be used for disease diagnosis. In this respect the invention is particularly advantageous over traditional diagnostic means where a biological constituent—typically of the blood—is measured and simply compared against the normal distribution of the population. What is missed in that approach is that the disease may manifest as a subtler imbalance in one or more biological components (e.g., serum proteins) that do not exceed the normal distribution of the population. Accordingly, a model is trained in 900 with reference multivariate observations of constituent quantities or expression levels (gene expression levels, protein content, metabolite content, etc.) exhibited by normal, healthy subjects. This reference data should cover a range of dynamic biological and metabolic normal conditions. In step 905, measurement data from one or more samples from a patient are provided for the same constituents. In step 910, the model generates estimates of constituents, as described elsewhere herein, responsive to the input of the patient's data. In step 920, the estimates and actual measured values from the patient are differenced to produce residuals. Keep in mind, though a particular constituent may be measured in the patient to exhibit a value well within the normal distribution of such measurements for the population, the residual for this constituent may be large, if the value the constituent should have taken on was different than expected in the estimate of the model. In step 924, the residuals are tested to make a determination whether the patient has a specific disease or not. This can be done in a number of ways, even in ways parallel to traditional methods. So, for example, where traditionally a disease may be diagnosed by measuring a constituent and determining the value thereof lies outside the normal distribution for the population, then according to the invention a disease may be diagnosed by testing a residual for a constituent (as produced with the model) and determining it lies outside the distribution of residuals expected for the healthy population (which can be ascertained by accumulating a distribution of residuals for normal subjects with this same inventive procedure), or more generally that the residual for a constituent lies above or below a critical threshold. In the event that the disease is more complex, it's diagnosis according to the invention may be performed by examining residuals for multiple constituents, or alternatively examining the residuals for a constituent for a time series of samples from the patient. In yet another embodiment, the pattern of residuals can be matched to patterns of residuals known to be associated with a specific disease. Residuals have both magnitude and direction (e.g., lower than expected or higher than expected), and patterns of residuals for diagnostic purposes can be formed in a variety of ways. For example, the pattern can be as simple as a "hi-lo" scheme, where each constituent residual is indicated to be either above normal, below normal or normal. In another example, the magnitude of the residual can be used to form a vector of residuals which can be pattern-matched according to a variety of known techniques for general pattern matching, such as a "nearest neighbor" approach. The residual pattern is tested for matching against a stored pattern or plurality of patterns associated with a disease or plurality of diseases, and if the match is found, a diagnosis can be made that the patient is exhibiting the disease.

Further according to the invention, the diagnostics exemplified in FIG. 9 can be applied to disease progression, or prognostics, as well. Residuals generated for one or more constituents can be measured against a progression scale that has been previously determined for known progressions of the disease using the model-based residuals of the present invention. Alternatively, the progression can be determined using the above-described residual pattern matching, whereby the residual pattern is matched to the closest progression class exemplified by residual patterns for that progression state. Likewise, the prognostic outlook for a patient's condition can be made based on the residual of a constituent, on the residuals of a plurality of constituents, or by residual pattern matching. For example, the prognosis for a given disease can be stratified into a plurality based on residual patterns for prior known cases of the disease and outcomes, and the present patient residual pattern matched against these for the closest match, indicating the likely prognosis. Of critical importance is the advantage afforded by the model-based residuals in differentiating biological expression levels or constituent quantities that subtly but reliably relate to disease state, which measurements would otherwise not be amenable to traditional methods merely comparing the quantity to a population mean and distribution.

Figure 3:
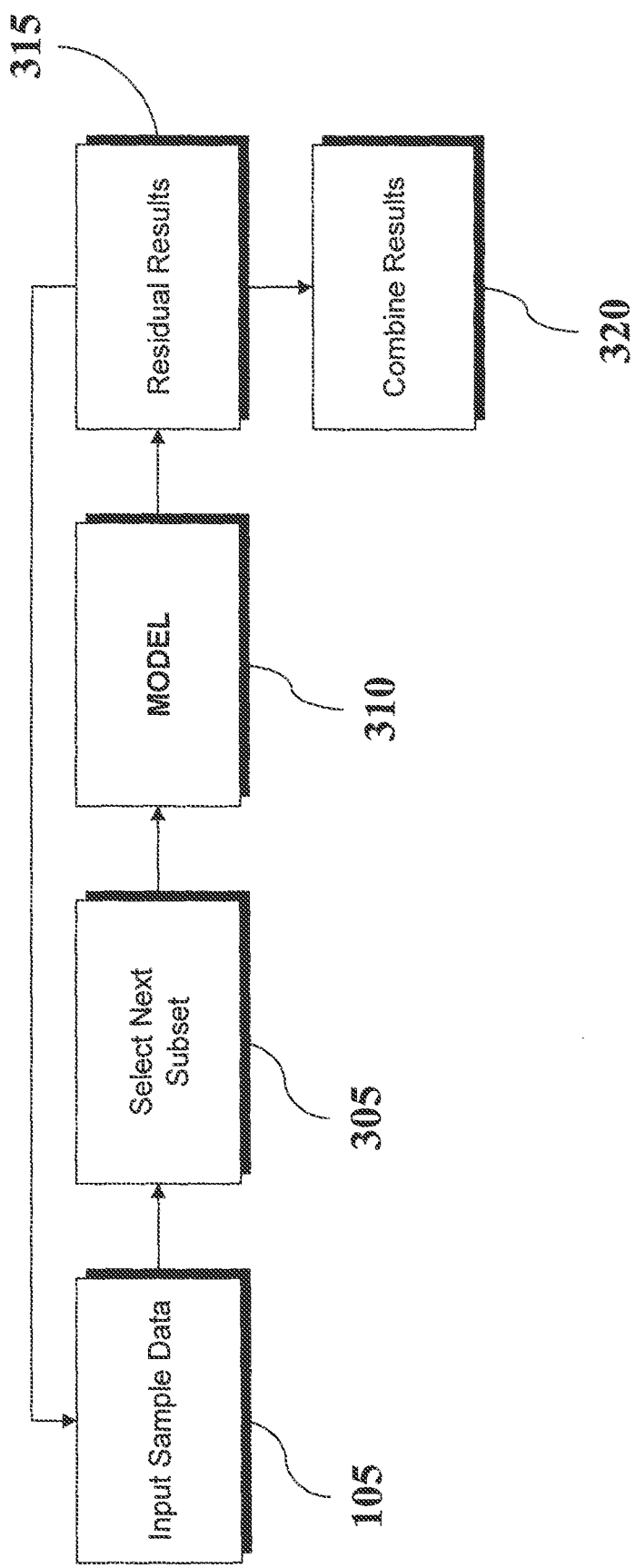
FIG. 3 is a flowchart of an iterative process according to the invention for mining omic data for biomarkers.

Turning to FIG. 3, the methodology of FIG. 1 can be extended to processing large sets of transcriptomic data to mine for biomarkers, in an iterative process. In step 105, the same sample vector is input, which may comprise 10,000 gene expression levels. In step 305, a subset of that set is filtered out for processing, which may be filtering for 100 feature genes at a time. The example 100 feature genes are then processed in step 310 through the model, where 310 represents the appropriate optional normalization step, autoassociative modeling step, residual generation step and residual test step as described with respect to FIG. 1. The results of this iteration are stored in step 315. Then the process is repeated with another set of features selected from the input in 305. In each iteration, an appropriately trained model corresponding to the feature genes selected is used in the modeling step 310. When all the iterations are complete, and all the desired input genes have been processed, the results are combined to identify the biomarkers across the 10,000-gene input. By breaking the modeling up into smaller chunks, the model is better able to track deviations. In a preferred embodiment, genes are selected with overlap in step 305, so that a genetic component can be modeled in more than one model, and in combination with different sets of genes taken, e.g., 100 at a time. By performing many iterations of subsets of data from the input sample, each genetic component has a statistical likelihood of being modeled in combination with genes which are part of its regulatory network, and which it is likely to have some kind of expression level relationship with. In step 320, then, results for genes are combined across all iterations, and it is determined statistically which genes had consistent indications of deviations. Thus, genes may be selected as biomarkers that have consistently shifted residuals; or that exhibited extremely large deviations in one or some of the iterations they were involved in, irrespective of how they performed in other iterations. Of course the above iterative search procedure can be extended for any sets of constituents, such as proteins, metabolites, and the like.

Turning now to the model, a number of techniques may be used to capture and model the relationships between genetic components to the extent they exist as biological pathways and networks of gene regulatory products. The model technique according to the invention must provide for multivariate autoassociative estimation, and must be capable of working without time/sequence information, since the sample inputs are typically from distinct patient samples and have no known time element. Preferably, the modeling technique is empirical. One class of models appropriate for the invention is the class of kernel-based models, exemplified by the equation:

$$x_{est} = \sum_{i=1}^{L} c_i K(x_{new}, x_i) \quad (2)$$

where the autoassociative estimate vector Xest is generated from a weighted sum of results from a kernel function K, which compares the input vector Xnew to learned patterns of expression levels, Xi. Kernel function K is a generalized inner product, but preferably has the further characteristic that its absolute value is maximum when Xnew and Xi are identical. The learned patterns come from the class on which the model is trained. One form of kernel-based model suitable for the present invention is the Nadaraya-Watson kernel regression, adapted for autoassociative output:

$$x_{est} = \frac{\sum_{i=1}^{L} d_i K(x_{new}, d_i)}{\sum_{i=1}^{L} K(x_{new}, d_i)} = \frac{D \cdot (D^T \otimes x_{new})}{\sum (D^T \otimes x_{new})} \quad (3)$$

where di represents the training pattern vectors (equivalent to Xi above), and comprises the training matrix D, and the kernel can be selected from a set of similarity operators ⊗ which are described further herein. In this case, the weights c are based on the sum of the kernel results themselves.

In a preferred embodiment, the kernel-based model is a similarity-based model (SBM), which in its autoassociative form is given by:

$$x_{est} = \frac{D \cdot (D^T \otimes D)^{-1} \cdot (D^T \otimes x_{in})}{\sum ((D^T \otimes D)^{-1} \cdot (D^T \otimes x_{in}))} \quad (4)$$

or alternatively, doing away with normalization by the weights:

$$x_{in} = D \cdot (D^T \otimes D)^{-1} \cdot (D^T \otimes x_{in}) \quad (5)$$

Again, the D matrix is the set of learned patterns, each vector comprising the expression level data for a plurality of genetic and/or protein components (and/or other metabolites). Uniquely, the weights c are determined in SBM in part by calculating the self-similarity inherent in the D matrix, where each vector in D is compared using the similarity kernel to every other vector in D. SBM is a particularly robust estimator, especially effective for noisy transcriptomic data.

The similarity operator is a type of kernel, which compares the input vector (e.g., Xin above) to another vector (e.g., one of the learned vectors Xi) and generates a scalar score from the comparison. Generally, in terms of a similarity score, the result should range between two boundary values (e.g., from zero to one), and when the input vectors are identical, the value of one of the boundary values should be returned, and as the vectors become increasingly dissimilar, the similarity score should approach the other boundary. One example is the Gaussian operator given by:

$$s = e^{-\frac{|x_{in} - x_i|}{h}} \quad (6)$$

where h is a "width" parameter that scales the response, and the function changes with N-dimensional distance between the vectors. At one extreme, when the vectors are identical, the response is one, and as the vectors become increasingly different, the similarity s drops off toward zero. Other boundary values may be used as the scale of similarity, and other similarity operators can be used. As another example, the similarity may be calculated on an elemental basis, that is, by calculating a similarity score for each pair of corresponding elements of the vectors, and then averaging the elemental similarity scores to produce a vector-to-vector similarity score. For example, the similarity may be:

$$s = \frac{1}{N} \sum_{i=1}^{N} \left( \left[ 1 + \frac{[(_A x_i - _B x_i)/R_i]^\lambda}{C} \right]^{-1} \right) \quad (7)$$

where N is the number of gene expression or protein components in each vector, $_A X_i$ is the element from one of the vectors, and $_B X_i$ is the corresponding element from the other vector, and R is a range associated with each component, which can be determined from the training data. The factors λ and C are scaling factors that can be used to tune the model, but in the default case, can be set to one.

Figure 4:
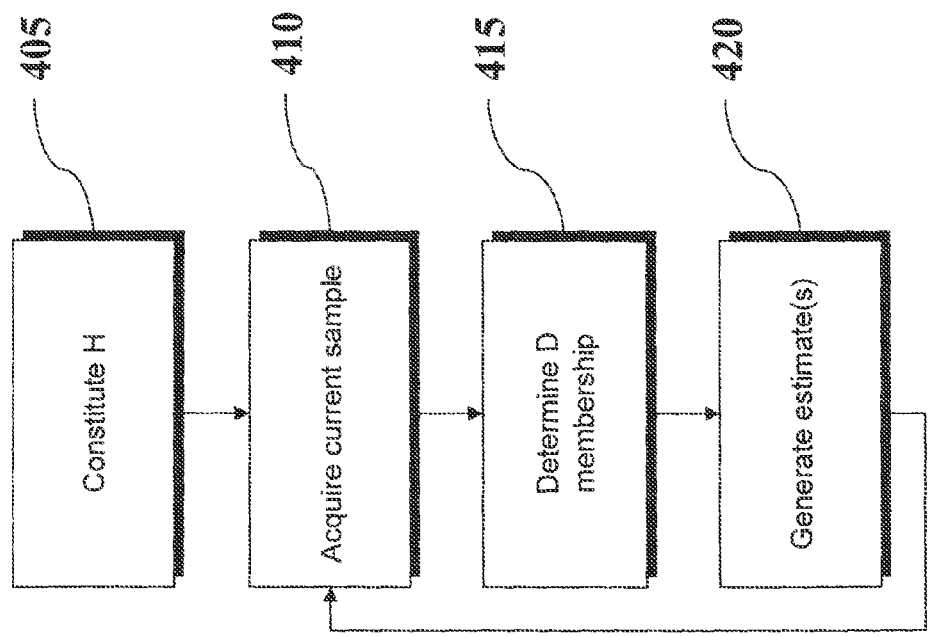
FIG. 4 is a flowchart of a method according to the invention for generating localized models based on the input.

In a preferred embodiment of the invention, localization is used to recreate the model with each new sample. Accordingly, turning to FIG. 4, the process of generating estimates is shown to include the reconstitution of the model based on the input sample. The training samples that comprise the Xi in the above discussion now are used to constitute a potentially large pool of training samples H, in step 405. The current sample is input to the modeling process in step 410. Based on that sample, a subset of the training set H is selected to comprise the matrix D described above, in step 415. Finally, using this localized D matrix specific to this input sample, the estimates are generated in step 420 as described above with respect to FIGS. 1 and 3 and with respect to the above equations. By doing localization, many extraneous samples are excluded from diluting the efficacy of the model, and only the most relevant observations are included in the model. This is extremely useful, for example, in view of the fact that transcriptomic samples represent a mere instant snapshot of cellular activity in a dynamic, living system. While a large library of patient samples may be assembled to provide learning patterns for the model, only a subset of those may represent the cellular behavior appropriate for the input sample at the moment it was acquired, and localization is key to generating a relevant empirical model on-the-fly. Kernel-based models are exceptionally well suited for this kind of localization because they are trained in one pass and can be updated rapidly.

A variety of criteria can be used to constitute the localized D matrix membership, including the similarity operator itself. Hence, according to one embodiment of the invention, the input vector can be compared to the library H of stored samples, and a similarity s can be calculated for each comparison. This provides a ranking of the stored samples, and a certain top fraction of them can be included in the D matrix. In a preferred embodiment of this localization aspect, vectors in the ranked list for H are included to the extent they provide a value for one of the transcriptome components that "brackets" the corresponding value in the input vector. This search down the ranked list is performed until either all values in the input vector are bracketed on both the low and high side, or until a maximum limit of vectors to include in D is reached. Other slight modifications in determining the membership of localized D are within the scope of the invention.

Figure 5:
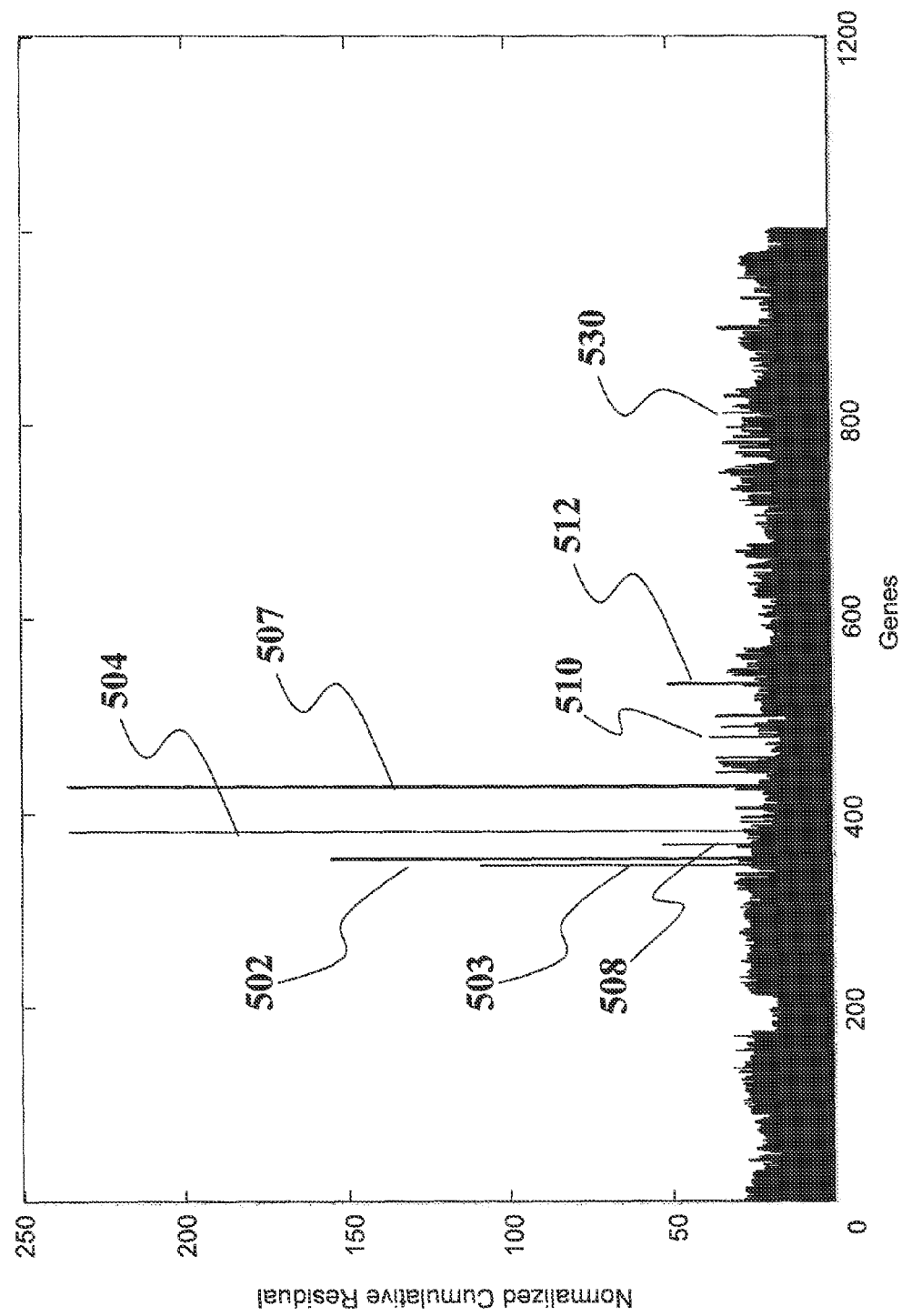
FIG. 5 is a bar chart of normalized cumulative residuals for simulated omic components, as produced by model-based analysis according to the invention.

Turning to FIG. 5, the results of an analysis are shown for 1000 genes in a similarity-based model with localization. The bars each show the normalized cumulative residual for each of the 100 genes, for a simulated set of genomic expression data. Each of the genes labeled 503, 504, 507, 510 and 512 were set to be "bad actors" in the genomic data, changing their dynamic behavior to simulate some form of breakdown of expression regulation. Genes 502 and 508 were tightly coupled with bad actor genes in a simulated regulatory network, and hence evidenced a signature of pathway breakdown as well. In contrast, the general background normalized cumulative residuals 530 were substantially lower. A simple threshold can be applied to generate a list of candidate biomarkers, or all the genes analyzed can be ranked based on a residual test, for further investigation. Because the kernel-based modeling approach used in the invention is fast to retrain, one can run alternative models with different feature sets and compare results, more rapidly discovering potential biomarkers, and advantageously highlighting previously unknown biological pathways and regulation networks.

Figure 6:
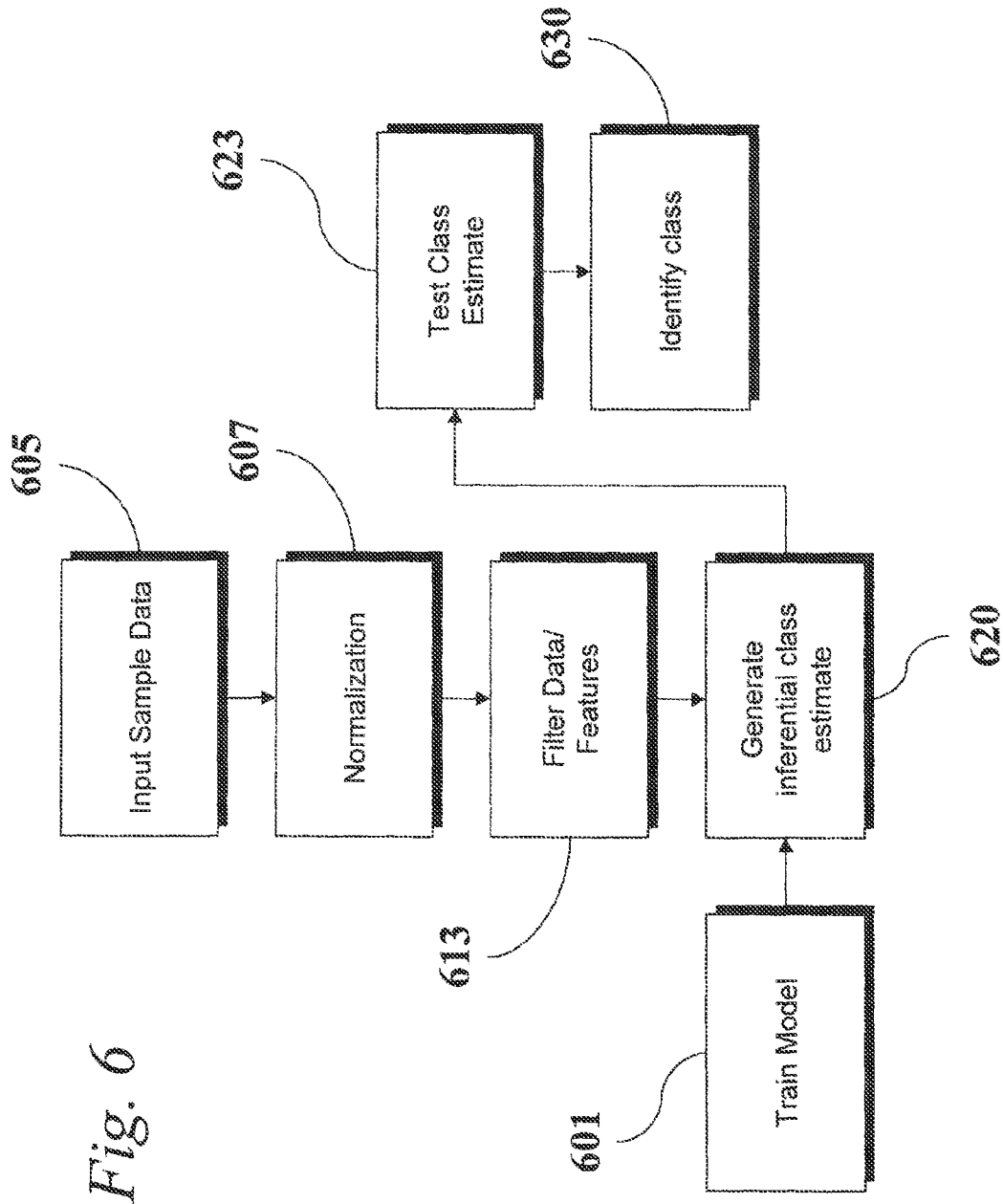
FIG. 6 is a flowchart of an inferential method according to the invention for diagnosis or prognosis of a disease condition based on'omic profiles.

Turning now to FIG. 6, a flowchart is shown of another aspect of the present invention for use in diagnostics and prognostics. This aspect of the invention is useful when a clinical determination of disease state is needed, either to detect the presence or absence of disease, or to distinguish which form of a disease is present, or which state of progression is evidenced. Accordingly, in step 601, a model is trained using prior-obtained expression level data representative of two classes, including a class variable, for example a "1" for class 1 and "−1" for class 2. In clinical practice, then, in step 605 a test sample is provided, for which a classification determination is desired.

In optional step 607, the expression level data is normalized, to remove experiment-to-experiment variation. As mentioned above, the data can be normalized using scaling according to the mean and standard deviation of the expression levels in a given patient sample. It may be preferable to perform the normalization prior to the filtering step 613, because it will better reflect the overall baseline of the sample input experiment to use all the genomic components in the normalization, rather than just selected/filtered features. Hence, in this FIG. 6 in contrast to FIG. 1, the normalization step is shown prior to the filtering step, to demonstrate that filtering and normalization can be performed in either sequence, as makes sense, according to the invention.

In optional step 613, the data may be filtered, for example to choose certain feature genes as a subset of the total number of expression levels available in the input sample. (However, it should be noted that in a clinical setting, it is likely an appropriately down-sized microarray will have been tailored to the clinical test, and will have only the feature genes on it that are useful for the particular classification. Hence, the input sample may have expression level data for only a dozen or two dozen probes.) The signal-to-noise ratio score is a commonly used ranking for genomic feature selection and can be used in the present invention to filter a subset of expression levels for classification. The signal-to-noise scores are determined from the training data that was used to train the model, and is shown above.

In step 620, the input sample is used by the model to generate an inferred variable, the class, of the input sample. The model is "inferential" in the sense that the class variable is not one of the inputs, as would be the case in an "autoassociative" model. Whereas the class variable in the training data is typically a discrete value (e.g., "1" or "−1"), the estimate directly from the model itself will be a continuous variable over the span of the discrete class variable range.

In step 623, the estimate of the class variable is tested. Since the class estimate is a continuous variable, there is a need to "discretize" the outcome. In the simplest form, the estimated class can be thresholded, and is assigned the discrete class that it is closer to. With class variables "1" and "−1" this would be equivalent to a threshold at zero. Alternatively, the threshold can be something other than the midway point between the discrete values, if this is for example warranted by the statistical distribution of class estimates made on the training data as a test. Accordingly, the distribution of estimates for the training data can be used to establish a threshold that optimally separates the two distributions. A further possibility is to calculate a likelihood of membership function for each distribution, and test the input sample class estimate with these membership functions.

In step 630, the classification of the input sample is output to the clinician or user. The output may be accompanied by a confidence assigned from the membership functions of the two distributions.

The model used in classification is again preferably an empirical model as described above, and more preferably a kernel-based model. In contrast to the autoassociative case, the model for classification must take an inferential form (this form is also used for residual generation with inferential models, described hereinabove). Generally, the kernel-based methods will take the form:

$$\hat{y} = \sum_{i=1}^{L} c_i K(x_{new}, x_i) \qquad (8)$$

where in this case an inferred variable or vector of variables y is determined from a comparison of a set of trained (learned) multivariate observations $x_i$ to the input observation $x_{new}$ using a kernel operator. These results are combined linearly according to the weights $c_i$ to yield the result. In kernel regression, a form of smooth estimator, the kernel equation takes the form:

$$\hat{y} = \frac{\sum_{i=1}^{L} d_i^{out} K(x_{new}, d_i^{in})}{\sum_{i=1}^{L} K(x_{new}, d_i^{in})} = \frac{D_{out} \cdot (D_{in}^T \otimes x_{new})}{\sum (D_{in}^T \otimes x_{new})} \qquad (9)$$

where $d_i$ are the learned vectors, and D is the matrix of such vectors. The kernel is represented by the operator ⊗ in the second form of the equation above. What kernel regression amounts to is that the weights c have become the D vectors normalized by the sum of the kernel comparison values. The training matrix D has been split into two sections for the inferential form, the first Din being those elements corresponding to expression level data, and Dout being those elements corresponding to the classification assigned to the expression level data. Hence, with genomic components in rows, and the last row being "class", and training samples in columns, Din would be all rows above the last row, and Dout would be a vector of the last row, the class variable.

Most preferably, a similarity-based model is used. Similarity-based modeling has a different form of the weights c as described above, and in the inferential form is used as:

$$y = \frac{D_{out} \cdot (D_{in}^T \otimes D_{in})^{-1} \cdot (D_{in}^T \otimes x_{in})}{\sum (D_{in}^T \otimes D_{in})^{-1} \cdot (D_{in}^T \otimes x_{in})} \quad (10)$$

$$y = D_{out} \cdot (D_{in}^T \otimes D_{in})^{-1} \cdot (D_{in}^T \otimes x_{in}) \quad (11)$$

where the division by the sum has been dropped (used when the data is normalized 0 o 1). In other words, the kernel results in SBM are normalized by the self-referential similarities of the training vectors themselves. SBM is a robust interpolator, and will ignore noise variables that might otherwise influence its ability to estimate variables evidencing real interrelationships.

The output can be an inferred variable y (Dout comprises the output classification yi associated with the training vectors), or an inferred multivariate vector y (again, Dout comprises the output vectors yi associated with the training vectors). According to the classification embodiment of the invention summarized above, the model is an inferential model that predicts the class variable y, which may take on two values in the training data, and the estimate of which will range between those two values. (In the above-described generation of residuals using an inferential model, it is inferred constituent estimate(s) that are generated instead of the classification estimate).

According to the invention, localization can be used in the inferential modeling process. The D matrix can be reconstituted on-the-fly based on the input observation. This is described above.

Figure 7:
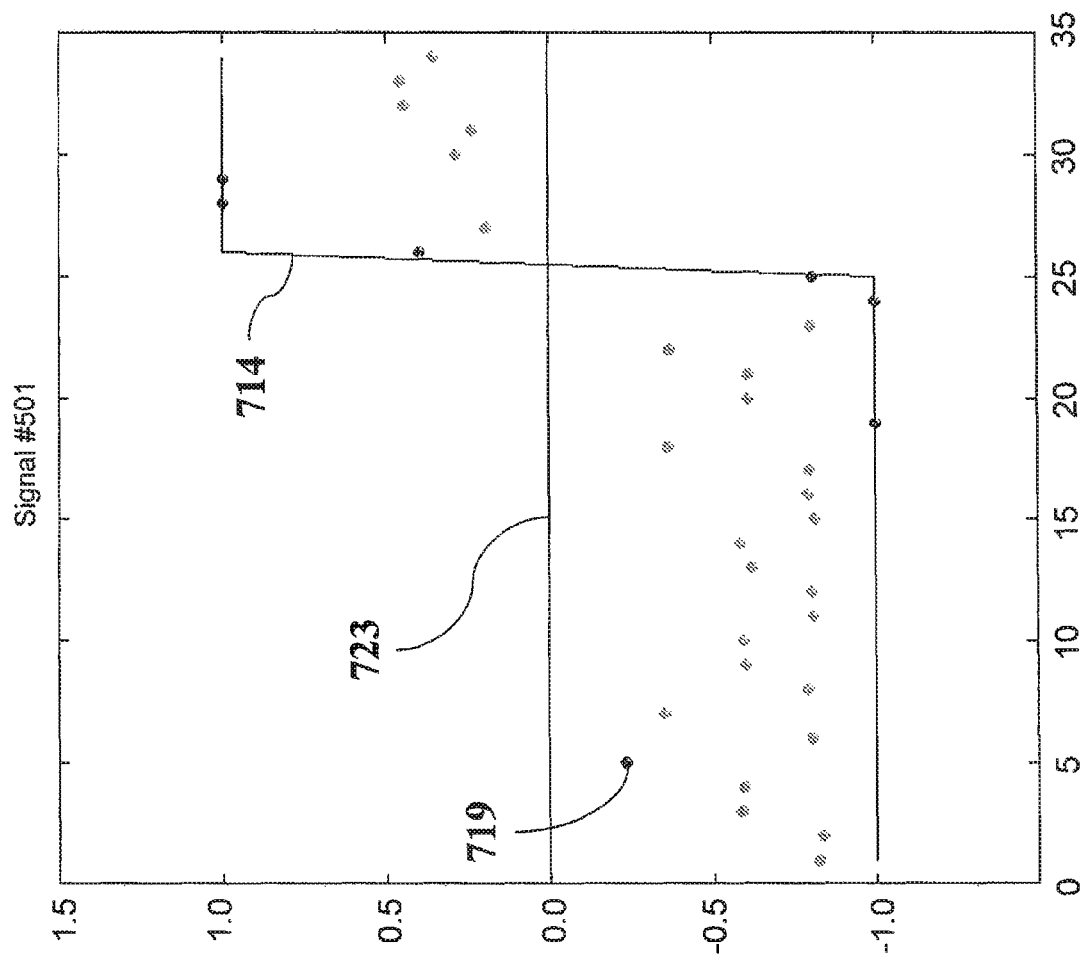
FIG. 7 is a chart showing inferential classification results (green) for prostate cancer genomic expression level data, using a method according to the invention.

Turning to FIG. 7, an example is shown of classification for prostate cancer expression level data. Training data consisted of 500 top ranked genomic components based on S2N scores, from a panel of 12,600 mRNA probes in a microarray of prostate tissue. 102 training samples trained the model, comprising approximately half from each of the two classes of "normal" and "cancerous" tissues. The expression level data was normalized by scaling according to mean and standard deviation in each sample. Line 714 shows the known classification of the 34 test samples, where class 1 has been assigned a value of 1 and class 2 has been assigned a value of −1. A localized SBM model was used to generate classification estimates, shown as dots 719. A threshold 723 at zero reveals that the model correctly estimated all 34 results. Such a result can be used clinically for real patient samples to provide a diagnosis.

Figure 8:
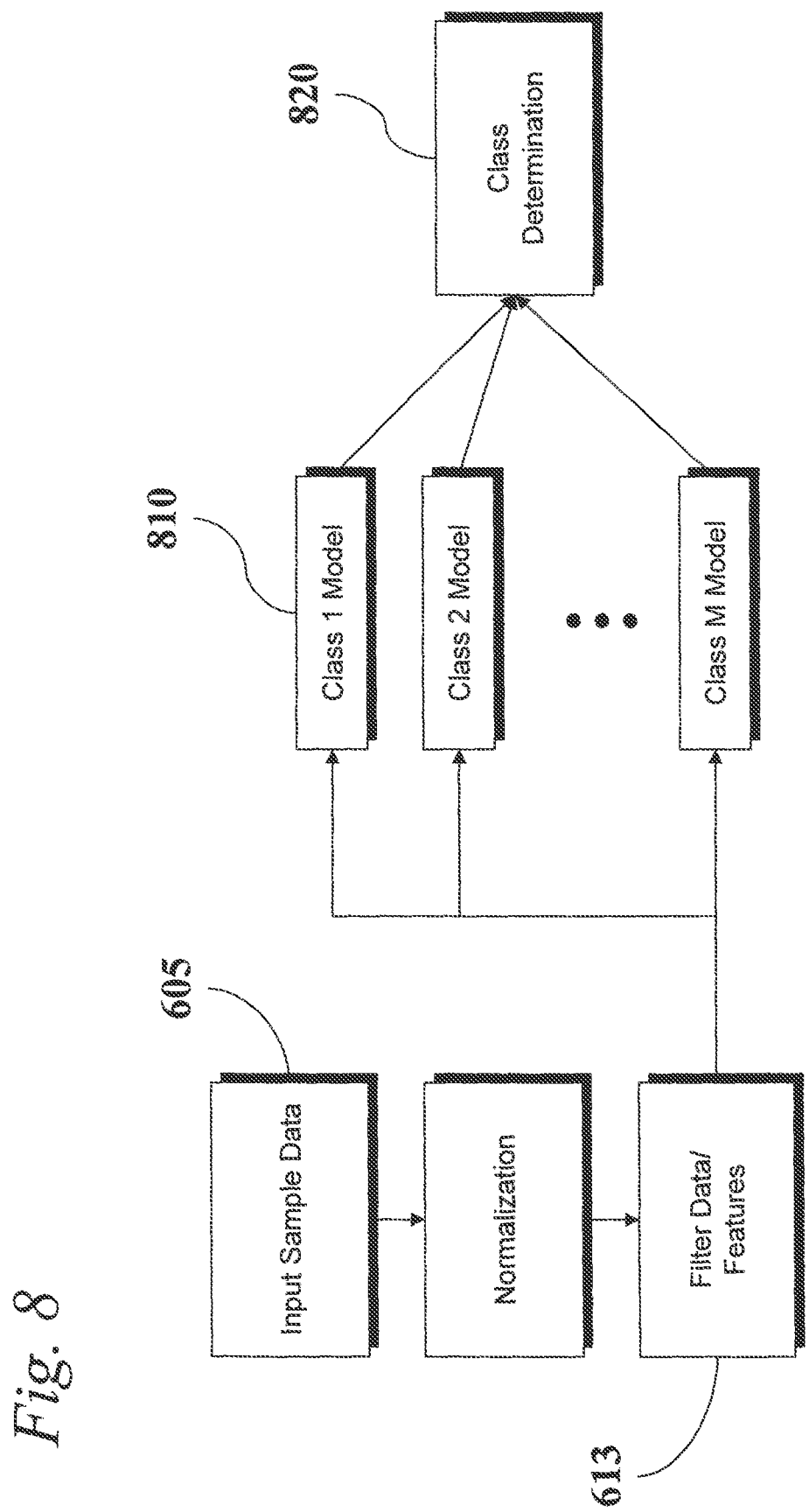
FIG. 8 is a flowchart of a multi-class method according to the invention for diagnosis or prognosis of a disease condition based on omic profiles.

Turning to FIG. 8, an alternative embodiment of the diagnostic aspect of the present invention is shown for use in multiple classifications, as when the sample input must be classified among several different alternatives. This is especially useful for prognostics, where multiple disease stages are characterized. Accordingly, instead of a single kernel-based or similarity-based model trained on examples from two classes, in FIG. 8 a bank 810 of M models is provided, each of which is trained only on data from a certain class selected from M classes. Furthermore, each model is not inferential, but rather autoassociative, as described above. The "class" variable does not need to be included, and is instead merely associated with each model. Each model receives as input the same sample input vector from optional step 613, or may receive an input customized for the features relevant to that classification, in which case filtering and/or normalization would occur as required for each model in 810 separately. The output of each model is an autoassociative estimate of the inputs to that model, namely the transcriptomic expression levels that comprised the input vector to it. Then, a similarity operator is used to compare the estimate vector to the actual input vector in each case to provide a "global similarity" score:

$$S_{global} = (x_{estimate}^T \otimes x_{in}) \quad (12)$$

The global similarity scores from a set of models can be compared in step 820 to determine the actual classification of the input. For example, the highest global similarity score may designate the classification of the input vector.

However, the global similarity from each model is preferably normalized so that the global similarities can be meaningfully compared. For example, one way is to normalize the global similarity from a model according to its general global similarity mean and variance for known classification in its class. This general mean and variance of the global similarity can be provided by doing leave-one-out modeling of the training set, for example. One class model may have typical global similarities at 0.97 mean and little variance, while the next maybe at 0.84 and large variance. The actual measured global similarity can be scaled to this mean and variance to provide a normalized score. For example, the score can be the difference between the actual measured value and the mean, divided by the variance. Other calculations for normalizing are well known and can be used. For example, the distribution of general global similarity scores can be modeled with a kernel regression and the actual measured global similarity converted to a probability score related to how likely it is the measured similarity belongs to the distribution associated with that model.

The present invention can take the form of a software product, either loaded on a workstation for processing local data, or on an application server on the web for processing data sent to it ("ASP" mode). In the workstation mode, the software may provide an environment for analyzing data produced from another software package, such as gene chip analysis software from vendors of microarrays, such as Affymetrix and Agilent, whether by loading files exported by those systems, or being called from those systems and receiving data directly from them. The processing environment is similar to a batch analysis workbench, for loading data from files and running alternative analyses on the data, and reporting and graphics functions. In the ASP mode, there may additionally be a large data repository on the back end of the system that stores a large amount of data from which a wide variety of disease-condition models have been trained. A facility for receiving new data to be analyzed or classified serves the input to the appropriate model (user selectable, or selectable by an automated algorithm) to provide the classification output or residual-based disease diagnosis or prognosis. A number of algorithms might be used to determine which models to employ against the incoming data in the absence of user selection. Often, however, this is dictated by the gene expression targets selected in the input microarray experiment or test.

In a clinical setting, the software may be loaded on a workstation as part of an apparatus for large scale patient sample testing. Tailored microarrays fit for testing particular disease conditions may be used to provide expression levels for just a handful of previously identified components of the disease signature, and these expression levels are processed in the workstation software to determine diagnosis or prognosis as described above in a number of alternative embodiments. Alternatively, large microarrays may be used for broad panel testing for disease, in which case the software may run the multi-classification modeling against the data. In the context of a mass spectrometry device, quantification of constituents is provided to the workstation software from the mass spectrometry control system or via exported files, which can then generate model-based residuals for biomarker identification, or for disease diagnosis/prognosis, using models either stored locally, or downloaded or otherwise accessed via an Internet connection. For example, a diagnostic lab may use the present invention in software to analyze the constituent quantities determined through mass spectrometry from a patient sample for a plurality of constituents, whereby a set of constituent residuals is generated for at least some of the measurements for purposes of diagnosis. The model that is used to generate the residuals can be a model specific to the disease test being run, in terms of the constituents modeled together or in terms of the type of reference data used to train the model. Disease diagnosis can be performed based on the residuals, e.g., a residual pattern. Residual patterns indicative of the specific disease can be stored locally, or can be accessed over the Internet from a large repository of such patterns. Further, the results of the patient test can be uploaded (for example, later upon further disease confirmation) to improve the accuracy of the online repository, and further tune the model and/or the residual patterns indicative of disease. Diagnostic results are reported from the software to screen and/or to a printed report, and can be served to a web page or to a fax number at a physician's office as is known in the art.

It will be appreciated by those skilled in the art, that modifications to the foregoing preferred embodiments may be made in various aspects. The present invention is set forth with particularity in the appended claims. It is deemed that the spirit and scope of that invention encompasses such modifications and alterations to the preferred embodiment as would be apparent to one of ordinary skill in the art and familiar with the teachings of the present application.

What is claimed is:

1. A method for discovery of biomarkers indicative of a medical condition in a species of organism, from a candidate set of molecular constituents extracted from such organisms, comprising the steps of:
   determining a set of molecular constituents to test as biomarkers;
   obtaining first measurements of the quantity of each of the molecular constituents present in each of a first plurality of samples extracted from such organisms free of the condition;
   training and storing in a computer memory, a kernel-based estimation model using said first measurements as multivariate training observations, each multivariate observation comprising the measurements from a single condition-free sample;
   obtaining second measurements of the quantity of each of the molecular constituents present in each of a second plurality of samples extracted from such organisms free of the condition;
   obtaining third measurements of the quantity of each of the molecular constituents present in each of a third plurality of samples extracted from such organisms having the medical condition;
   estimating with said model, using a microprocessor, an estimated quantity for each of at least some of the molecular constituents in a sample, responsive to inputting to said model a multivariate input observation comprising the measurements from that sample, for all of said second plurality of samples and all of said third plurality of samples;
   computing residuals corresponding to at least one molecular constituent, each residual being the difference between an estimated quantity of that molecular constituent for a sample and the measured quantity of that molecular constituent for that sample; and
   comparing, for at least one molecular constituent, residuals from said second plurality of samples with residuals from said third plurality of samples, to identify whether that molecular constituent is a biomarker of said medical condition.

2. A method according to claim 1, wherein said residual comparing step further comprises comparing, for at least one molecular constituent, the mean of residuals from said second plurality of samples with the mean of residuals from said third plurality of samples.

3. A method according to claim 1, wherein said residual comparing step further comprises comparing, for at least one molecular constituent, the standard deviation of residuals from said second plurality of samples with the standard deviation of residuals from said third plurality of samples.

4. A method according to claim 1, wherein said residual comparing step further comprises determining, for at least one molecular constituent, the ratio of the difference of the mean of residuals from said second plurality of samples with the mean of residuals from said third plurality of samples, to the sum of the standard deviation of residuals from the second plurality of samples and the standard deviation of residuals from the third plurality of samples.

5. A method according to claim 1, wherein said molecular constituents are selected from the set of the proteome and metabolome of the said organisms.

6. A method according to claim 5, wherein said first and second measurements are determined by mass spectrometry.

7. A method according to claim 1, wherein said kernel-based estimation model is a similarity-based model.

8. A method according to claim 1, wherein said kernel-based model comprises a set of reference multivariate observations selected from the set of multivariate observations formed from said first measurements, and wherein said step of estimating with said model comprises localized estimation that uses only a subset of the set of reference multivariate observations, selected for each sample as a function of the multivariate input observation.

9. A method according to claim 7, wherein said similarity-based model uses a similarity operator that determines similarity on an elemental basis.

10. A method according to claim 9 wherein said similarity operator generates similarity values on an elemental basis as a function of the range expected for each constituent.

11. A method for diagnosing a medical condition in a suspect biological specimen, comprising the steps of:
   storing in a computer memory a kernel-based estimation model comprising multivariate observations of first measurements of the quantity of each of a set of molecular constituents present in each of a first plurality of samples extracted from multiple biological specimens free of the condition, each multivariate observation comprising the measurements from a single condition-free sample;

obtaining second measurements of the quantity of each of the molecular constituents present in said suspect biological specimen;

estimating with said model, using a microprocessor, an estimated quantity expected for each of at least some of the molecular constituents in said suspect biological specimen, responsive to inputting to said model a multivariate input observation comprising said second measurements from said suspect biological specimen;

computing a residual corresponding to each of at least one molecular constituent, each residual being the difference between the estimated quantity of that molecular constituent and the measured quantity of that molecular constituent; and testing said residuals to determine if said suspect biological specimen has said medical condition.

12. A method according to claim 11, wherein said residual testing step further comprises comparing each residual of a molecular component to an expected distribution of residuals for that molecular component determined from model estimates made in the same manner for a second plurality of samples from biological specimens free of the condition.

13. A method according to claim 12, wherein said molecular constituents are selected from the set of the proteome and the metabolome of the biological specimens.

14. A method according to claim 13, wherein said suspect biological specimen in a sample of blood serum.

15. A method according to claim 14, wherein said kernel-based estimation model is a similarity-based model.

16. A method according to claim 11, wherein said kernel-based model comprises a set of reference multivariate observations selected from the set of multivariate observations formed from said first measurements, and wherein said step of estimating with said model comprises localized estimation that uses only a subset of the set of reference multivariate observations, selected as a function of the multivariate input observation of the suspect biological specimen.

17. A method according to claim 15, wherein said similarity-based model uses a similarity operator that determines similarity on an elemental basis.

18. A method according to claim 17 wherein said similarity operator generates similarity values on an elemental basis as a function of the range expected for each constituent.

19. A method according to claim 11, wherein said residual testing step further comprises the steps of:

storing in said computer memory residuals for at least some of the molecular components determined from model estimates made in the same manner for a second plurality of samples from biological specimens free of the condition;

storing in said computer memory residuals for at least some of the molecular components determined from model estimates made in the same manner for a third plurality of samples from biological specimens having the condition;

applying a nearest neighbor test, using said microprocessor, to determine whether said residuals from said suspect biological specimen are better matched to the residuals from said second plurality of samples or to the residuals from said third plurality of samples to diagnose the medical condition.

20. A method according to claim 11, further comprising the step of displaying the determination of whether said suspect biological specimen has said medical condition on a computer display.

21. A method according to claim 11, further comprising the step of transmitting the determination of whether said suspect biological specimen has said medical condition via fax.

* * * * *